United States Patent [19]
Pinto et al.

[11] Patent Number: 5,476,017
[45] Date of Patent: Dec. 19, 1995

[54] UNIT DOSE BULK MATERIAL SAMPLING APPARATUS

[75] Inventors: Ivan Pinto, West Chester, Pa.; Gerardo Perez, Elkton, Md.; William P. Wallace, Pedricktown, N.J.

[73] Assignee: Acutrol Co.

[21] Appl. No.: 136,139

[22] Filed: Oct. 15, 1993

[51] Int. Cl.⁶ ........................................ G01N 1/04
[52] U.S. Cl. ........................ 73/864.62; 73/864.63
[58] Field of Search .......................... 73/864.13, 864.16, 73/864.44, 864.45, 864.62, 863.84, 864.13, 864.18, 864.17, 864.63, 863.81, 864.41, 864.64, 864.51, 863.82, 864.91; 422/100

[56] References Cited

U.S. PATENT DOCUMENTS

| | | |
|---|---|---|
| 176,038 | 4/1876 | Nelson . |
| 455,733 | 7/1891 | Bell . |
| 2,844,036 | 7/1958 | Wright ........................ 73/425.4 |
| 3,080,760 | 3/1963 | Piersma ....................... 73/425.2 |
| 3,158,109 | 11/1964 | Stott ................................ 107/17 |
| 4,023,716 | 5/1977 | Shapiro ....................... 73/864.14 |
| 4,056,360 | 11/1977 | Risch ........................... 73/864.17 |
| 4,141,251 | 2/1979 | Oshikubo .................... 73/864.18 |
| 4,148,315 | 4/1979 | Berezkin et al. ............ 73/864.18 |
| 4,172,385 | 10/1979 | Cristensen .................. 73/425.4 R |
| 4,640,614 | 2/1987 | Roberts et al. .................. 356/36 |
| 4,840,517 | 6/1989 | Bullivant ........................... 175/20 |
| 5,272,926 | 12/1993 | Wilkins ....................... 73/864.16 |
| 5,343,771 | 9/1994 | Turriff et al. ............... 73/864.44 |

FOREIGN PATENT DOCUMENTS

| | | | |
|---|---|---|---|
| 0259260 | 9/1988 | European Pat. Off. | ......... G01N 1/00 |
| 1505827 | 3/1978 | United Kingdom | ............. G01N 1/28 |

OTHER PUBLICATIONS

Pharmaceutical Technology, Mar. '92 p. 136 showing advertisement for Bulk Powder Sampling apparatus.

Primary Examiner—Hezron E. Williams
Assistant Examiner—Nashmiya N. Ashraf
Attorney, Agent, or Firm—Breneman, Georges & Krikelis

[57] ABSTRACT

Apparatus for removing a sample of granular or powder materials from a vat in which such materials are mixed in bulk, including an elongated probe having a sample receiving cavity at one end which may be adjusted to a predetermined volume. The probe is inserted in the bulk mixture to a predetermined depth, the cavity loaded with material from the bulk and after closing the cavity, the probe is removed from the bulk removing therefrom a sample of a desired predetermined quantity representative of the bulk mixture at the insertion point. A backing plate is also provided in the probe to compact the sample in the cavity to facilitate handling of the sample.

12 Claims, 2 Drawing Sheets

UNIT DOSE BULK MATERIAL SAMPLING APPARATUS

BACKGROUND OF THE INVENTION

1. Field of the invention

This invention relates to apparatus for sampling bulk granular or powder material, and more particularly to an apparatus for unit dose sampling of mixed bulk material.

2. Description of Related Art

Sampling of bulk mixtures of granular or powdery materials to evaluate the degree of mixing at different locations in a mixing vessel is typically done using a probe or sample thief which is inserted in the bulk mixture to remove a representative sample therefrom. The probes comprise a long tubular shell having at least one aperture on a side wall near the lower end of the probe, and a second inner mating tube also having at least one aperture which can be caused to match the opening in the outer tube by rotating the inner tube within the outer tube. The probe is inserted in the bulk mixture to the desired depth, with the inner tube positioned so that the opening in the inner tube is not aligned with the opening in the outer tube. After insertion of the tube to a desired depth, the inner tube is rotated to align the two openings, allowing bulk material to flow in the opened inner tube. The opening is then closed by again rotating the inner tube, and the probe removed from the bulk material retrieving a sample of the material from a desired point in the mixing vessel. The sample retrieved is recovered from the probe for further analysis or study as needed.

Such bulk sampling apparatus suffers from an inability to sample an accurate and representative sample of the bulk material since there is very little, if any, control of the amount of material that will flow in the probe, so that an accurate and repeatable sample may be obtained and tested.

An improved bulk powder sampling probe, particularly for use in the Pharmaceutical industries where the precise and complete mixing of powdery substances is essential in order to produce uniform content pills, is the SAMPCO Bulk powder Sampler, marketed by the SAMPCO-LANTZ CONSULTANTS of 1 Ripple Court, Keowee Key, Salem, S.C. 29676. This sampler, advertised as a unit sampler uses probes with different capacity sampling chambers, varying in size from 1, 1.5 and 2 cc., providing samples that contain approximately the same amount of powder as corresponds to a single dose of the particular medication, or a small multiple thereof. This apparatus also employs a double tube type arrangement whereby the sampling cavity is filled from the side of the probe, and after filling, is closed for sample retrieval. Thus it is still subject to repeatability errors since filling occurs from the side. In addition, as the sample size decreases, the sampling accuracy further suffers from the difficulty to assure complete recovery of the retrieved sample from the sampling cavity. When the sample is small, any material adhering to the cavity walls becomes a larger proportion of the total sample, introducing variations in the sampled material that may and often do substantially effect the test results. In addition recovery of the powder from the side opening by tapping the probe against the wall of a receiving container results of some powder becoming airborne and lost, as well as some remaining in the cavity, further decreasing the sampling accuracy.

There is thus still a need for an apparatus able to recover predetermined size samples from mixing bulk materials with a high degree of repeatability of the sample size, with minimal disturbance of the bulk material in the sampling vicinity and with the ability to recover substantially all of the retrieved sample from the sampling apparatus in a format easily amenable to further testing.

These and other objects of the present invention will be clear from the following description.

SUMMARY OF THE INVENTION

In accordance with the present invention there is provided an apparatus for unit dose bulk material sampling, comprising:

an elongated housing having a length, an axis coextensive with said length, a first bore extending along said axis the length of said housing, an open front end lying in a plane substantially perpendicular to the axis, and a back end;

a moveable piston supported in said first bore, comprising a plug having a front surface lying in a plane perpendicular to the axis and a shaft extending from said plug in a direction opposite said front surface along said axis, the plug sized to fit the first bore to form a sampling cavity in the first bore extending between the front surface of the plug and the open front end of the housing;

means operable to axially move said piston for selectably varying the position of the plug in the first bore thereby changing the size of the cavity; and a closure cap attached to said housing for selectably opening and closing said open front end. The closure cap can be rotated between a first position sealing the entrance to the cavity and a second position opening the entrance to the cavity.

The means for axially varying the position of the piston, and thus the size of the cavity include a thumb screw extending through the housing into the bore, and the shaft extending from said plug includes a threaded portion in the vicinity of said screw, with the tip of the screw riding on the threaded potion of the shaft.

The apparatus further comprises compacting means for applying an axial force on the piston with the closure cap in the first position to forcibly displace the piston in the bore in the direction of the opening, thus compacting the material in the cavity. The piston can be moved again in the same direction with the closure cap in the second, open, position, to expel the material from the cavity.

Further adjustment of the cavity may be provided by providing the housing with a demountable and replaceable front section with an open front end, said front section having a second bore (smaller or larger than the first bore) extending therethrough, the second bore also extending along the housing axis, and wherein the piston plug is also replaceable and is sized to fit the second bore, and wherein the demountable front section open front end is sealed and opened by the closure cap.

BRIEF DESCRIPTION OF THE DRAWINGS

The invention can be more fully understood from the following description thereof in connection with the accompanying drawings described as follows.

DESCRIPTION OF THE PREFERRED EMBODIMENTS

Figure 1:
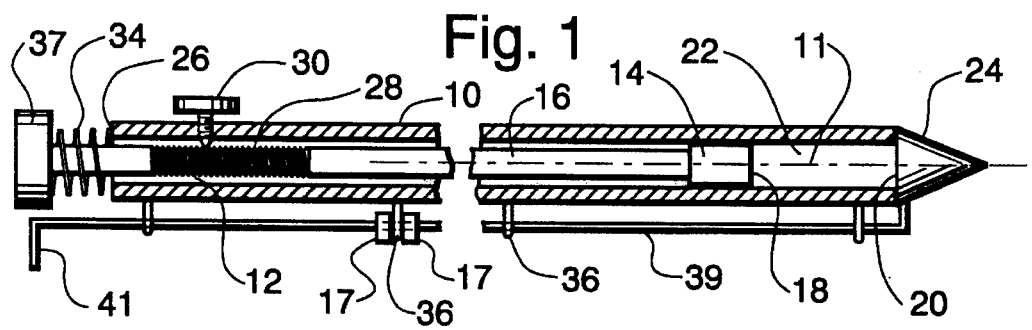
FIG. 1 is a representation in schematic cross section of an elevation view of an apparatus in accordance with the present invention.

Throughout the following detailed description, similar reference characters refer to similar elements in all figures of the drawings.

Figure 3:
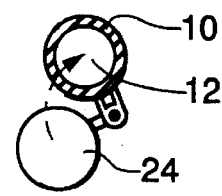
FIG. 3 is a schematic representation of the view of the apparatus of FIG. 2 taken along line "3—3"
Figure 2:
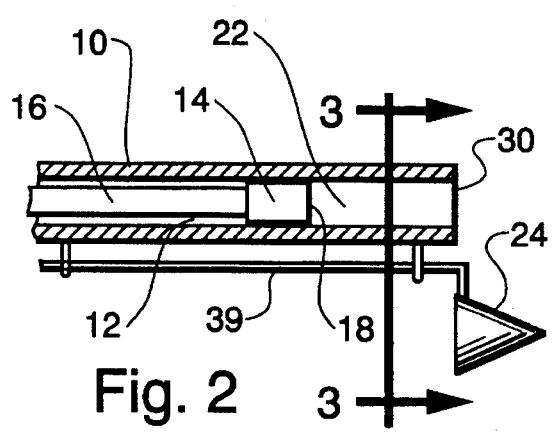
FIG. 2 is a representation in schematic cross section of an elevation view of the front end portion of the apparatus of FIG. 1 with the closure cap in the open position

Referring now to FIGS. 1, 2, and 3, there is shown an apparatus in accordance with this invention. The apparatus, referred to herein after as the "probe", comprises an elongated housing 10 which is preferably cylindrical in shape having an axis 11 extending along the long dimension of the housing. The housing 10 is hollow, having a bore 12 extending therethrough. Bore 12 is also preferably cylindrical and lies coaxially with the housing along axis 11. One end of the housing defined as the front end 20 is open, while the other end defined as the back end 26 is closed. The front end is open and the opening is contained in a plane perpendicular to the axis 11.

Within the housing 10 in the bore 12 rides a piston comprising a plug 14 and a shaft 16 extending from the plug. The piston is supported in the bore so that it can move along the axis 11. The plug is sized to completely fit inside the bore 12 so that the plug wipes the inside of the bore as it moves along the axis 11. The shaft 16 extends outside the housing 10 through an opening in the back end 26 of the housing. This opening supports one end of the piston in the bore, the other end being supported by the plug which slides within the bore. The combined length of the shaft 16 and plug 14 comprising the piston, is longer than the length of the housing 10.

The plug on the side opposite from the shaft, ends in a front surface 18 which lies in a plane perpendicular to the axis 11. The front surface 18, the inside walls of the bore 12 and the front end 20 of the housing 10 define a sampling cavity 22 whose total volume is varied by moving the plug 14 along the axis 11. Typical cavity volumes for unit dose sampling as used by the Pharmaceutical industry are in the range of 1 to 5 cubic centimeters. However these dimensions are illustrative rather than limiting and a probe built in accordance with the present invention may provide cavity sizes substantially different than those mentioned, the cavity size depending primarily on the application and sample size desired.

A closure cap 24 of generally frusto-conical shape having a pointed end and a base is mounted near the front end of the housing. The closure cap is mounted on the housing through a cam rod 39. Cam rod 39 has one end connected to the base of the closure cap 24. Cam rod 39 is attached to the housing 10 through at least two supporting struts 36. The struts support the rod 39 so that the rod can rotate around its axis but cannot move axially. This is obtained by having at least one set of collars 17 placed on either side of at least one strut 36 on the cam rod 39 as shown in FIG. 1. The other end of the rod terminates to a cam handle 41. Preferably, the orientation of the handle 41 is such as to indicate at a glance whether the closure cap is in the open or closed position. This may be readily done by aligning the handle along a line extending from the rod axis in the base of the closure cap to a point representing the projection of the apex of the frusto-conical closure cap onto the base. Other indicating arrangements may of course be used, the above described one being preferred because of its simplicity.

Figure 9:
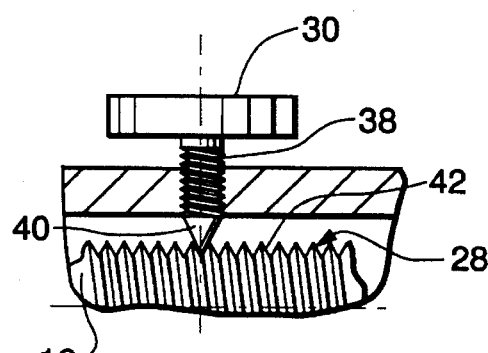
FIG. 9 is a schematic elevation cross section of a portion of the apparatus showing in detail the thumb screw and shaft thread arrangement which provide an alternate way to control the position of the piston.

The shaft 16 includes a threaded portion 28. A thumb screw 30, better shown in FIG. 9, has a threaded body 38 which extends into bore 12 through a matching threaded opening in the housing 10. The screw body terminates to a generally pointed tip 40 which is sized to ride in the grooves of threads 42 of threaded portion 28 of shaft 16. A spring 34 located between the housing back and a thumb wheel 37, as shown in FIG. 1, exerts axial pressure on the thumb wheel 37 and shaft 16, and forces one side of the threads 42 against the thumb screw tip 40, preventing movement of the shaft along axis 11. Rotation of the thumb wheel 37 causes the thumb screw tip to ride on the groove of the threads 42 and, since the thumb screw tip position is fixed in the housing, such rotation displaces the shaft along the axis 11, also axially displacing the plug and changing the size of the cavity 22. By selecting a fine pitch for the threads 42, and a fine point for the tip of the thumb screw, very fine adjustments of the cavity volume are possible. Tightening of the thumb screw 30 against the shaft 16 after adjustment of the volume of cavity 22, prevents the accidental disruption of a selected setting. A set screw operating on the thumb screw 30 (not illustrated) may also be used to further prevent accidental changes in the selected setting.

Figure 4:
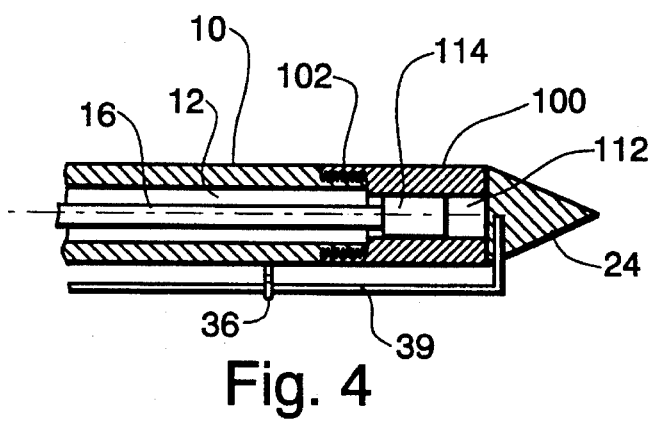
FIG. 4 is a representation in schematic cross section of an elevation view of the front end of an apparatus having replaceable front end sections in accordance with a different embodiment of the present invention.

FIG. 4 shows another embodiment of the present invention, in which the housing front end is replaceable by a small housing section 100 which contains a bore 112 which is of a different size than the bore 12 in the main housing. This second bore 112 is so located that when the housing section 100 is mounted on housing 10, the first bore 12 and the second bore 112 are coaxial. A replaceable plug 114 is also threaded to the shaft 16 to fit in the new bore size. The housing portion 100 is preferably attached to housing 10 by screwing the housing portion 100 to the end of housing 10 on threads 102. Preferably the outer diameter of the two housings is the same, resulting in a smooth outer surface for the complete housing. The replaceable housing 100 has a length and diameter such that closure cap 24 may remain in place and continue to function with each such replaceable housing.

Figure 5:
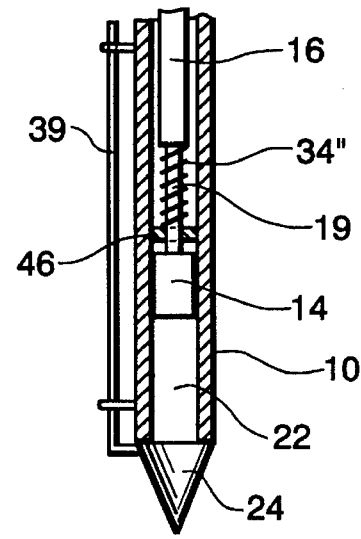
FIG. 5 is a representation in schematic cross section of an elevation view of the front end of an alternate apparatus in accordance with this invention showing a different placement of the pressure applying spring.

FIG. 5, shows yet another embodiment of the present invention, in which the spring 34" is not located externally, but is placed within the bore 12. An abutment 46 is placed inside the bore at a location such that it does not impede the travel of plug 14 to attain the desired maximum size cavity.

The shaft extends through a hole in this abutment. The shaft 16 in this embodiment may have a small section 19 of lesser diameter than the rest of the shaft. The diameter of spring 34" is selected to be less than the diameter of the main portion of shaft 16 but greater than the diameter of the shaft section 17, so as to fit over the shaft at that section. When assembled, the spring presses against the housing 10 through abutment 46, and urges the shaft 16 axially to apply the needed positive contact between the tip of thumb screw 30 and the threads 42 on the threaded portion 28 of the shaft 16 as discussed above.

Figures 6, 7, 8:
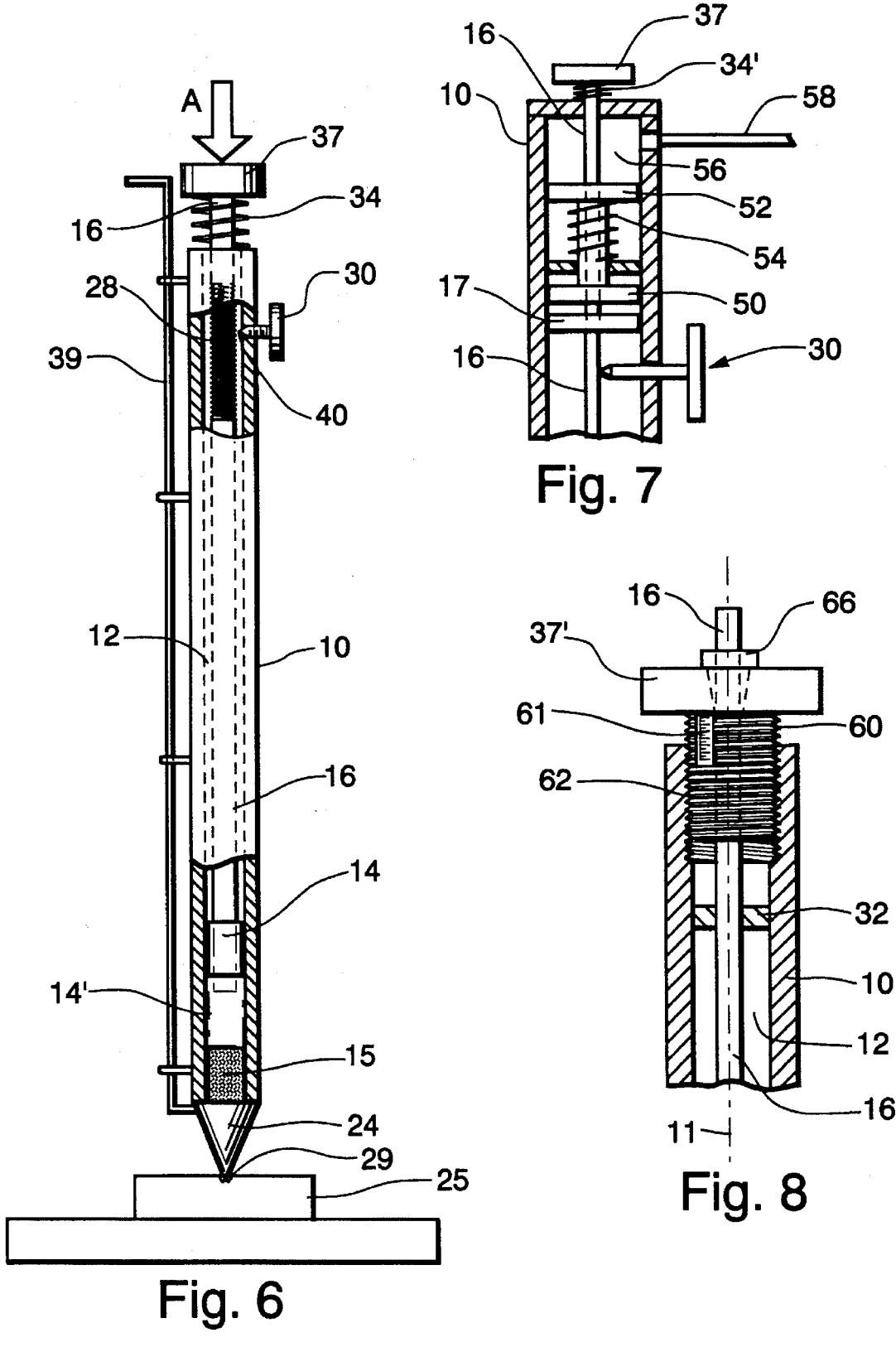
FIG. 6 is a partial cross sectional representation of the apparatus of FIG. 1 and the external backing plate as used for compacting a powder sample.
FIG. 7 is a representation in schematic cross section of the back portion of apparatus in accordance with the present invention showing an alternate embodiment for applying a compacting force to the piston.
FIG. 8 is a representation in schematic cross section of the back portion of apparatus in accordance with the present invention showing an alternate embodiment which includes a micrometer for adjusting the position of the piston.

Referring now to FIG. 6, there is shown the probe described above together with a backing plate 25 for use in compacting sampled bulk material retrieved in cavity 22. To achieve compacting, a backing plate 25 preferably having an indentation 29 for receiving the pointed end of closure 24 and preventing it from sliding is used. Means to apply a compacting force represented by arrow "A", which may be a hammer or other device which can be used to forcibly push the shaft 16 in an axial direction, is used to displace the piston along axis 11 in the bore, moving plug 14 to a position indicated as 14' and shown in phantom lines in FIG. 6 compressing and compacting into a pellet 15, the bulk sample retrieved in the cavity 22.

FIG. 7 shows an alternate compacting means. In this embodiment, the rear portion of the housing includes a chamber 56 within which rides a fluid actuated piston 52 which extends into bore 12. Shaft 16 includes an annular collar 17. Shaft 16 extends through the center of piston 52 and chamber 56 to outside of housing 10 and terminates in a thumb wheel 37 as for the prior embodiment. A spring 54 operates on piston 52 to urge such piston away from the shaft collar 17. Piston 52 has a strike plate 50 attached to its one end facing shaft collar 17. Sealing means not illustrated are provided to prevent the escape of fluid from the chamber to the bore in the housing, or to the exterior of the housing. In operation, when a compacting force is desired to be applied to a sample in the cavity, a driving fluid which can be air, from a source not illustrated, is directed under pressure through a conduit 58 into chamber 56 driving piston 52 against the force of spring 34', so that strike plate 50 impacts on shaft collar 17 forcing the shaft to move in the direction of axis 11, compacting the sample in the cavity.

FIG. 8 shows yet another embodiment of the present invention, in which the thumb screw 30 and threads 42 on the shaft 16 are replaced by a modified micrometer which serves as the back end of the housing. As shown, a schematically represented micrometer cylinder 60 having a threaded outer surface is inserted into a matching threaded rear portion 62 at the back end of housing 10. The micrometer cylinder 60 includes graduations 61 which are used to determine with a high degree of accuracy the displacement of the plug 14 in the bore and therefore by extension the size of the cavity. A thumb wheel 37' is used to turn the cylinder driving it in and out of the housing. The shaft 16 extends through the cylinder center above the cylinder, so that a compacting force may again be applied thereto, and is secured to the cylinder with a compression type set screw 66. This set screw 66 has a slightly conical body and a bore therethrough, through which passes the shaft. The screw body is scored and has threads on the outside surface. As the screw is threaded in the thumb wheel, because of the conical shape of the screw body the body is squeezed and the bore size becomes smaller, in effect clamping shaft 16 in position. Unscrewing the set screw 66 releases the shaft, allowing free movement in an axial direction to effect compacting of a sample. Means, such as indicator markings, may be provided on the shaft to allow resetting the shaft to a desired position in the micrometer cylinder. An optional shaft support 32 may be provided within the bore 12.

In operation, a probe constructed according to this invention, and more particularly one in accordance with the design shown in FIG. 1, is first adjusted to remove a predetermined size sample for testing. The size of the sample cavity 22 is adjusted for a particular size sample by rotating the thumb wheel and adjusting the position of the plug in the bore. The adjustment may be based on preestablished, calibrated settings marked on the housing, or may be done by trial and error by measuring the contents of the cavity and further adjusting the plug position to obtains the desired volume. Once the proper size has been established, the closure cap is placed in the first, closed position, sealing the opening to the cavity 22. The probe is then inserted into the bulk material to a desired depth from which a sample of the material is to be obtained. When the proper insertion point has been reached, the closure cap is rotated by rotating the handle 41 to the second position diametrically opposite the first position completely opening the front end 20 of the housing 10 and cavity 22. The probe is then pushed further into the bulk material by a small distance forcing bulk material into the cavity through the open front end. The closure cap is closed, sealing the cavity, and the probe removed from the bulk material.

Once the probe is removed from the bulk material, the next step depends somewhat on what type of material is sampled, and what type of testing will be performed. In the simplest case where the material is granular, and the particle size is large enough so that losses in the air during the process of emptying the sample in the test vessel are an insignificant proportion of the total, the sample is removed from the cavity, simply by opening the closure cap and letting the sample fall into the test vessel. To assure that all of the sample has emptied the thumb screw 30 securing the shaft in place is unscrewed to a degree that removes the screw tip from engagement with the threads 48. The shaft 16 is pushed from the back of the probe by pushing on the thumb wheel 37 to move the plug towards the open front end and to expel any material clinging on the cavity walls.

When the sample consists of powdery substances, as for instance is often the case for pharmaceutical applications, where the sample represents a unit dose corresponding to a particular medicinal pill composition, it is essential that all of the sample in the cavity be recovered, if an accurate analysis of the degree of component mixing in the sampling vicinity is to be obtained. In such instances, it is preferred that compaction of the sample prior to discharging the sample from the cavity take place. Prior to compaction, the thumb screw 30 is again backed out from engagement with the threads on the shaft so that the shaft may move freely along the axis 11. To effectuate compaction of the sample, the probe is placed with the closure cap tip against the backing plate. To prevent slippage of the probe during the compaction process, the closure tip of the probe is placed in the indentation in the backing plate. The probe is held in a position such that the axis 11 is substantially perpendicular to the backing plate, and using a small mallet or other similar implement, a compacting force is applied to the thumb wheel, moving the plug axially and compressing the sample as shown in FIG. 6. This results in compacting the sample within the cavity and forming a pellet 15. In pharmaceutical applications, because of the ability to both completely fill and empty the sampling cavity, and because of the ability to test the compacted sampled material without substantial further sample losses in the handling of the pelletized sample, the sample size can be adjusted with sufficient accuracy, so that the compacted pellet represents an equivalent single dose of a particular medication sampled.

Those skilled in the art having the benefit of the teachings of the present invention as hereinabove set forth, can effect numerous modifications thereto. The manner in which the micrometric adjustment of the plug position may vary as well as the way in which set screws may be used to secure the plug in a selected position. Indicators other than a micrometer type may be used to indicate the location of the plug. The application of the compacting force may be done in addition to the manners illustrated by other means, such as electromotive forces instead of fluidic. Stainless steel is a preferred material of construction for the probe, since it provides both strength and freedom from corrosion, however other materials including plastics may be used, so long as they provide the required structural strength for this the particular probe use.

These modifications are to be construed as being encompassed within the scope of the present invention as set forth in the appended claims.

We claim:

1. A sampler apparatus for unit dose bulk material sampling, comprising:

an elongated housing having a length, an axis coextensive with said length, a first bore extending along said axis the length of said housing, an open front end lying in a plane substantially perpendicular to the axis, and a back end;

a moveable piston supported in said first bore, comprising a plug having a front surface being in a plane perpendicular to the axis and a shaft extending from said plug in a direction opposite said front surface along said axis, the plug sized to completely fit the first bore to form a saddling cavity in the first bore having an adjustable sampling volume for containing a predetermined quantity of said bulk material, said sampling cavity extending between the front surface of the plug and the open front end of the housing, the open front end of the housing forming an entrance to the sampling cavity;

means operable to axially move said piston for selectively varying the position of the plug in the first bore for adjusting and presetting the size of the sampling cavity prior to sampling;

a closure cap attached to said housing and having means for selectively controlling opening and closing said entrance to the sampling cavity prior to, after and when the sampler is inserted in the bulk material for sampling.

2. The apparatus according to claim 1 wherein the means operable to axially move said piston for selectively varying the position of the plug in the first bore thereby changing the size of the cavity, include a micrometer.

3. The apparatus according to claim 1 wherein the means operable to axially move said piston for selectively varying the position of the plug in the first bore thereby changing the size of the cavity include a thumb screw extending through said housing into said bore, and wherein the shaft extending from said plug in a direction opposite said front surface along said axis, includes a threaded portion in the vicinity of said screw, and the screw has a tip riding on the threaded potion of the shaft.

4. The apparatus according to claim 3 further comprising spring means associated with said shaft for applying a force on said shaft in a direction along the axis whereby the threaded portion of the shaft is urged against the tip of the screw.

5. Apparatus according to claim 4 further comprising locking means acting on said piston for locking and preventing further movement of said piston within the first bore.

6. Apparatus according to claim 1 or 5 wherein the closure cap for the front end of sand housing is rotatably mounted on said housing for rotation between a first position sealing the entrance to the cavity and a second position opening the entrance to the cavity.

7. Apparatus according to claim 6 wherein said closure cap controlling means is mounted on said housing and connected to the closure cap for rotating said closure cap between said first and said second positions.

8. The apparatus of claim 6 further comprising compacting means for applying an axial force on said piston when the closure cap is in the first position to forcibly displace said piston in said bore in the direction of said opening, whereby bulk material in the cavity will be compacted.

9. The apparatus of claim 8 wherein the compacting means includes a fitted backing plate external to the housing.

10. The apparatus according to claim 6 wherein the housing includes a demountable and replaceable front section with an open front end, said front section having a second bore extending therethrough, the second bore also extending along the housing axis, and wherein the piston plug is also replaceable and is sized to fit the second bore, and wherein the demountable front section open front end is sealed and opened by the closure cap.

11. The apparatus according to claim 10, wherein the second bore has a diameter, said diameter being smaller than a diameter of the first bore.

12. The apparatus according to claim 10, wherein the second bore has a diameter, said diameter being larger than a diameter of the first bore.

* * * * *